(12) United States Patent
Prior et al.

(10) Patent No.: US 12,324,607 B2
(45) Date of Patent: *Jun. 10, 2025

(54) UTERINE MANIPULATOR WITH DETACHABLE CUP AND LOCKING OCCLUDER

(71) Applicant: Covidien LP, Mansfield, MA (US)

(72) Inventors: Scott J. Prior, Branford, CT (US); Danial P. Ferreira, Shelton, CT (US); Paul C. DiCesare, Easton, CT (US)

(73) Assignee: Covidien LP, Mansfield, MA (US)

( * ) Notice: Subject to any disclaimer, the term of this patent is extended or adjusted under 35 U.S.C. 154(b) by 790 days.

This patent is subject to a terminal disclaimer.

(21) Appl. No.: 17/553,927

(22) Filed: Dec. 17, 2021

(65) Prior Publication Data

US 2022/0104850 A1    Apr. 7, 2022

Related U.S. Application Data

(63) Continuation of application No. 15/593,594, filed on May 12, 2017, now Pat. No. 11,213,320.

(51) Int. Cl.
| | | |
|---|---|---|
| *A61B 17/42* | (2006.01) | |
| *A61B 17/00* | (2006.01) | |
| *A61B 90/00* | (2016.01) | |
| *A61B 90/30* | (2016.01) | |

(52) U.S. Cl.
CPC ...... *A61B 17/4241* (2013.01); *A61B 2017/00473* (2013.01); *A61B 2017/00557* (2013.01); *A61B 2017/00734* (2013.01); *A61B 2017/00849* (2013.01); *A61B 2017/00853* (2013.01); *A61B 2090/062* (2016.02); *A61B 2090/309* (2016.02)

(58) Field of Classification Search
CPC .......................... A61B 17/42; A61B 17/4241
See application file for complete search history.

(56) References Cited

U.S. PATENT DOCUMENTS

| | | |
|---|---|---|
| 4,597,030 A | 6/1986 | Brody et al. |
| 4,804,240 A | 2/1989 | Mori |
| 5,209,754 A | 5/1993 | Ahluwalia |
| 5,394,863 A | 3/1995 | Sanford et al. |
| 5,451,221 A | 9/1995 | Cho et al. |
| 5,487,377 A | 1/1996 | Smith et al. |
| 5,520,698 A | 5/1996 | Koh |
| 5,643,285 A | 7/1997 | Rowden et al. |
| 5,840,077 A | 11/1998 | Rowden et al. |
| 5,935,098 A | 8/1999 | Blaisdell et al. |
| 6,129,662 A | 10/2000 | Li et al. |
| 6,423,075 B1 | 7/2002 | Singh et al. |

(Continued)

FOREIGN PATENT DOCUMENTS

| | | |
|---|---|---|
| CN | 202489982 U | 10/2012 |
| CN | 202920313 U | 5/2013 |

(Continued)

*Primary Examiner* — Ryan J. Severson
(74) *Attorney, Agent, or Firm* — Carter, DeLuca & Farrell LLP

(57) ABSTRACT

A uterine manipulator includes a handle and a central shaft that extends distally from the handle. The central shaft includes a distal end portion supporting a balloon. The central shaft also supports a cervical cup. An occluder shaft is slidably supported on the central shaft. A non-inflatable plug is secured to the occluder shaft and configured to move with the occluder shaft as the occluder shaft slides along the central shaft.

20 Claims, 9 Drawing Sheets

(56) References Cited

U.S. PATENT DOCUMENTS

| | | |
|---|---|---|
| 6,516,216 B1 | 2/2003 | Fontenot et al. |
| 8,025,670 B2 | 9/2011 | Sharp et al. |
| 8,128,622 B2 | 3/2012 | Podhajsky et al. |
| 8,192,444 B2 | 6/2012 | Dycus |
| 8,206,357 B2 | 6/2012 | Bettuchi |
| 8,292,901 B2 | 10/2012 | Auerbach et al. |
| 8,298,213 B2 | 10/2012 | Singh |
| 8,323,278 B2 | 12/2012 | Brecheen et al. |
| 8,453,910 B2 | 6/2013 | Bettuchi et al. |
| 8,460,289 B2 | 6/2013 | Sartor |
| 8,528,563 B2 | 9/2013 | Gruber |
| 8,545,513 B2 | 10/2013 | Blair et al. |
| 8,603,105 B2 | 12/2013 | Sauer |
| 8,663,239 B2 | 3/2014 | Hess |
| 8,696,563 B2 | 4/2014 | Williams et al. |
| 8,784,410 B2 | 7/2014 | Dunning |
| 8,939,988 B2 | 1/2015 | Auerbach et al. |
| 9,011,433 B2 | 4/2015 | Batchelor et al. |
| 9,022,927 B2 | 5/2015 | Kleyman |
| 9,033,977 B2 | 5/2015 | Morozov |
| 9,066,724 B2 | 6/2015 | Jenkins |
| 9,101,390 B2 | 8/2015 | Singh et al. |
| 9,144,454 B2 | 9/2015 | Batchelor et al. |
| 9,392,935 B2 | 7/2016 | Adams et al. |
| 11,213,320 B2 | 1/2022 | Prior et al. |
| 2003/0187334 A1 | 10/2003 | Biswas |
| 2005/0085827 A1 | 4/2005 | G. et al. |
| 2006/0271037 A1 | 11/2006 | Maroney et al. |
| 2006/0291195 A1 | 12/2006 | Horrell et al. |
| 2008/0208210 A1 | 8/2008 | Blair et al. |
| 2010/0106163 A1 | 4/2010 | Blair et al. |
| 2010/0280524 A1 | 11/2010 | Lopez Zepeda |
| 2011/0130769 A1 | 6/2011 | Boebel et al. |
| 2011/0190689 A1 | 8/2011 | Bennett et al. |
| 2012/0016185 A1 | 1/2012 | Sherts et al. |
| 2012/0109147 A1 | 5/2012 | Auerbach et al. |
| 2012/0116416 A1 | 5/2012 | Neff et al. |
| 2012/0143210 A1 | 6/2012 | Brecheen et al. |
| 2012/0165826 A1 | 6/2012 | Rhemrev-Pieters |
| 2012/0283718 A1 | 11/2012 | Cosmescu |
| 2012/0323079 A1 | 12/2012 | Bakare et al. |
| 2012/0330324 A1 | 12/2012 | Sauer |
| 2013/0066328 A1 | 3/2013 | Singh et al. |
| 2013/0085508 A1 | 4/2013 | Hess |
| 2013/0110126 A1 | 5/2013 | Mujwid |
| 2013/0131459 A1 | 5/2013 | Williams et al. |
| 2014/0012305 A1 | 1/2014 | Horton et al. |
| 2014/0303641 A1 | 10/2014 | Boebel et al. |
| 2014/0358158 A1 | 12/2014 | Einarsson |
| 2015/0005780 A1 | 1/2015 | Einarsson |
| 2015/0080905 A1 | 3/2015 | Begemann et al. |
| 2015/0127016 A1 | 5/2015 | Sauer |
| 2015/0351621 A1 | 12/2015 | Hill et al. |
| 2016/0045757 A1 | 2/2016 | Groseth |
| 2016/0074186 A1 | 3/2016 | Sartor et al. |
| 2016/0095649 A1 | 4/2016 | Motai et al. |
| 2016/0100861 A1 | 4/2016 | Parys et al. |
| 2016/0100862 A1 | 4/2016 | Parys |
| 2016/0106463 A1 | 4/2016 | Egle et al. |
| 2017/0325844 A1 | 11/2017 | Prior |

FOREIGN PATENT DOCUMENTS

| | | |
|---|---|---|
| CN | 203244440 U | 10/2013 |
| CN | 203303125 U | 11/2013 |
| CN | 204446045 U | 7/2015 |
| CN | 204698659 U | 10/2015 |
| CN | 205072992 U | 3/2016 |
| DE | 102009018521 A1 | 10/2010 |
| EP | 2243437 A1 | 10/2010 |
| EP | 3865760 A1 | 8/2021 |
| WO | 03015643 A2 | 2/2003 |
| WO | 2008136024 A1 | 11/2008 |
| WO | 2011140604 A1 | 11/2011 |
| WO | 2012151622 A1 | 11/2012 |
| WO | 2013090909 A1 | 6/2013 |
| WO | 2016025132 A1 | 2/2016 |

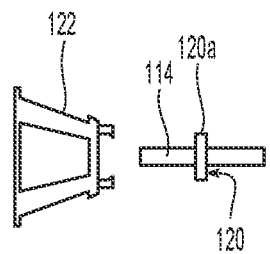 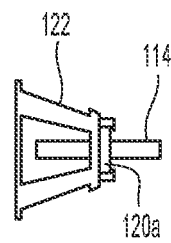
Fig. 10A          Fig. 10B
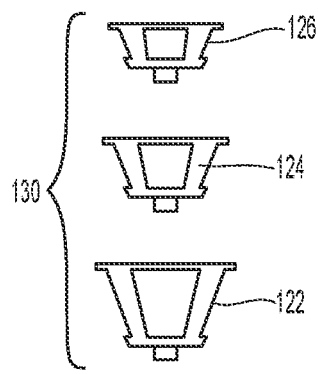
Fig. 11
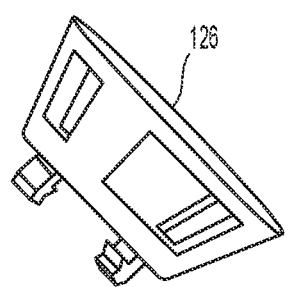          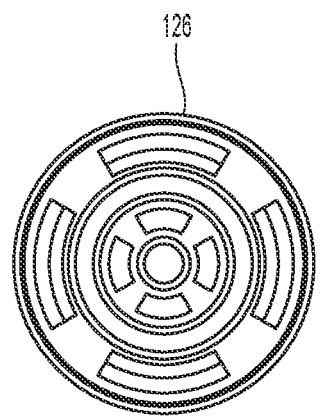
Fig. 12          Fig. 13

UTERINE MANIPULATOR WITH DETACHABLE CUP AND LOCKING OCCLUDER

CROSS REFERENCE TO RELATED APPLICATIONS

This application is a continuation of U.S. patent application Ser. No. 15/593,594, filed May 12, 2017, the entire contents of which are incorporated herein by reference.

TECHNICAL FIELD

The present disclosure relates to laparoscopic hysterectomy procedures and, more particularly, to uterine manipulators for performing a colpotomy procedure.

BACKGROUND

Colpotomy, one of the final steps in a laparoscopic hysterectomy, requires making a circular incision in vaginal tissue to separate the uterus from the vagina. This incision is typically performed with the aid of a uterine manipulator.

Uterine manipulators are conventionally used during laparoscopic hysterectomy procedures to mobilize and position the vagina and the cervix to facilitate separation and to enable removal of the uterus or other tissue specimens subsequent to performance of a colpotomy. Typically, uterine manipulators include a handle, a shaft extending distally from the handle, an inflatable balloon supported on the end of the shaft opposite the handle, and a cervical or colpotomy cup supported on the shaft proximally of the inflatable balloon. In use, the inflatable balloon is advanced through the vagina and cervix and is positioned within the uterus in a deflated position. Once positioned within the uterus, the inflatable balloon is inflated to secure the uterine manipulator within the uterus and the colpotomy cup is positioned about the cervix for effectuating the colpotomy.

SUMMARY

In accordance with an aspect of the present disclosure, a uterine manipulator is provided. The uterine manipulator includes a handle and a central shaft that extends distally from the handle. The uterine manipulator further includes a balloon supported on a distal end portion of the central shaft, a cervical cup supported on the central shaft, an occluder shaft slidably supported on the central shaft, and a non-inflatable plug secured to the occluder shaft and configured to move with the occluder shaft as the occluder shaft slides along the central shaft.

In some embodiments, the cervical cup may be selectively detachable from the central shaft.

In certain embodiments, the cervical cup may include one or more light emitting diodes.

In some embodiments, the uterine manipulator may include a shuttle slidably supported on the central shaft and selectively coupled to the cervical cup. The shuttle may include one or more tabs that are depressible to selectively couple the shuttle to the cervical cup. The cervical cup may include a ledge. The one or more tabs may be positioned to engage the ledge of the cervical cup to selectively secure the shuttle and cervical cup together. The cervical cup may include a raised ring that extends from the ledge and may be positioned to surround the one or more tabs.

In some embodiments, the central shaft may include a collar adjacent to the balloon. The collar may be positioned to engage the shuttle to prevent the cervical cup from sliding off the central shaft while the cervical cup is coupled to the shuttle.

In certain embodiments, the uterine manipulator may include a locking mechanism having a spring supported about the central shaft and positioned to selectively lock the occluder shaft to the central shaft to prevent the occluder shaft from sliding along the central shaft.

In some embodiments, the non-inflatable plug has a tapered configuration that is configured to be received within a vagina to occlude the vagina.

According to yet another aspect, a uterine manipulator includes a central shaft, a cervical cup, a shuttle selectively secured to the cervical cup and supported for slidable movement with the cervical cup along the central shaft, and a plug supported for slidable movement along the central shaft.

In certain embodiments, the plug may be positioned to slide along the central shaft independent of the shuttle.

In some embodiments, the cervical cup may be separable from the shuttle to enable the cervical cup to separate from the central shaft.

In certain embodiments, the plug may include a foam material.

In some embodiments, the plug may have a tapered configuration that is positioned to be received within a vagina to occlude the vagina.

In certain embodiments, the plug may have a frustoconical configuration.

In some embodiments, the cervical cup may include one or more light emitting diodes.

In some embodiments, the plug may be supported on an occluder shaft that is slidably mounted on the central shaft.

In certain embodiments, the occluder shaft may support a locking mechanism. The locking mechanism may support a torsion spring that selectively prevents the occluder shaft from sliding along the central shaft. The locking mechanism may include an actuator coupled to the torsion spring. The actuator may be positioned for actuation to tension the torsion spring and enable the occluder shaft to slide along the central shaft.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 10A is side view of a cervical cup of the uterine manipulator of FIG. 8 shown separated from a hub assembly of the uterine manipulator of FIG. 8;

FIG. 10B is a side view of the cervical cup of FIG. 10A coupled to the hub assembly of FIG. 10A;

FIG. 11 is a side view of a set of differently sized cervical cups;

FIG. 12 is an enlarged, perspective view of one of the cervical cups seen in FIG. 11; and FIG. 13 is a top view of the cervical cup of FIG. 12.

DETAILED DESCRIPTION

Figure 1:
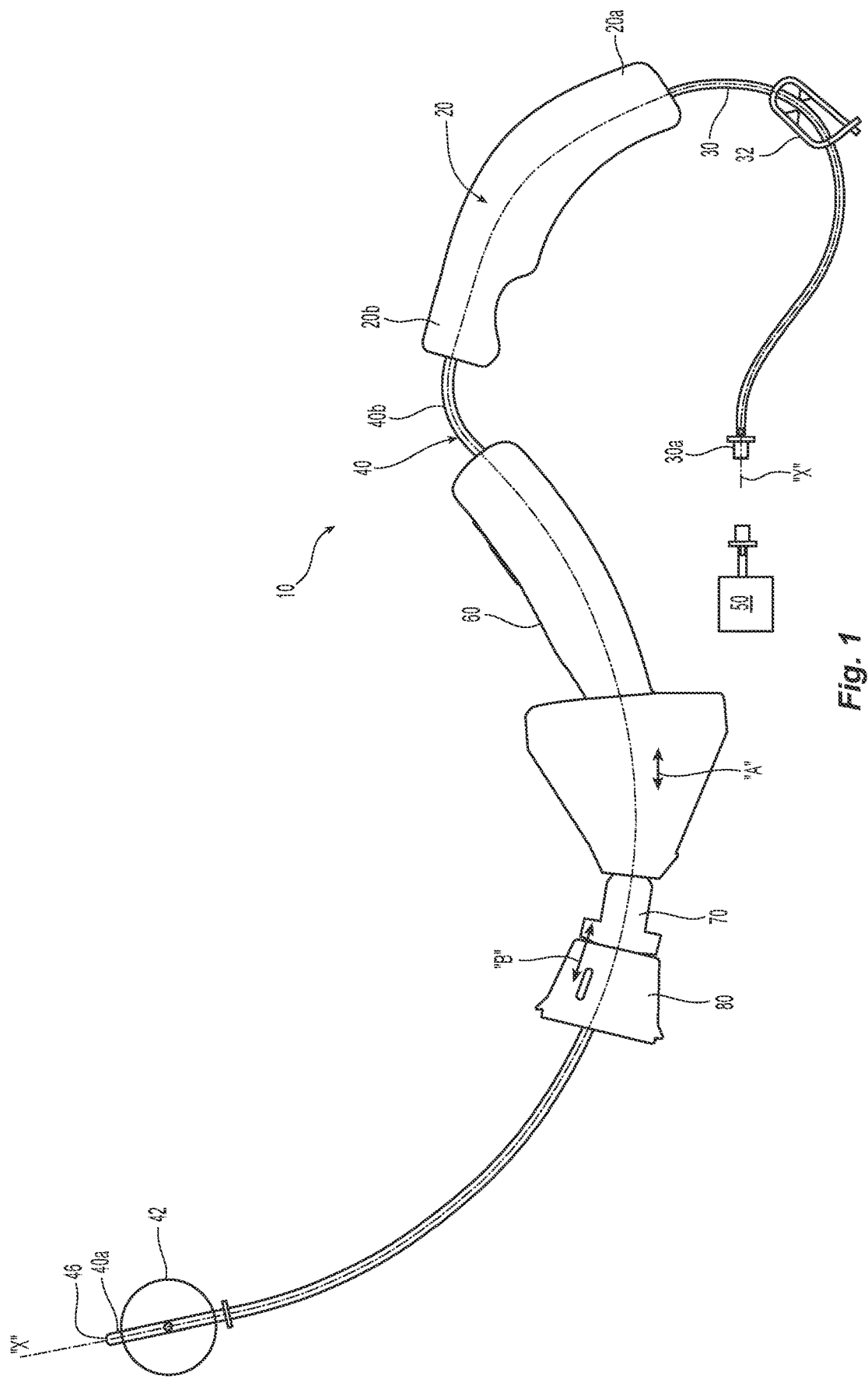
FIG. 1 is a perspective view of a uterine manipulator in accordance with the principles of the present disclosure.

Embodiments of the present uterine manipulators are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel.

In the following description, well-known functions or constructions are not described in detail to avoid obscuring the present disclosure in unnecessary detail.

Figure 2:
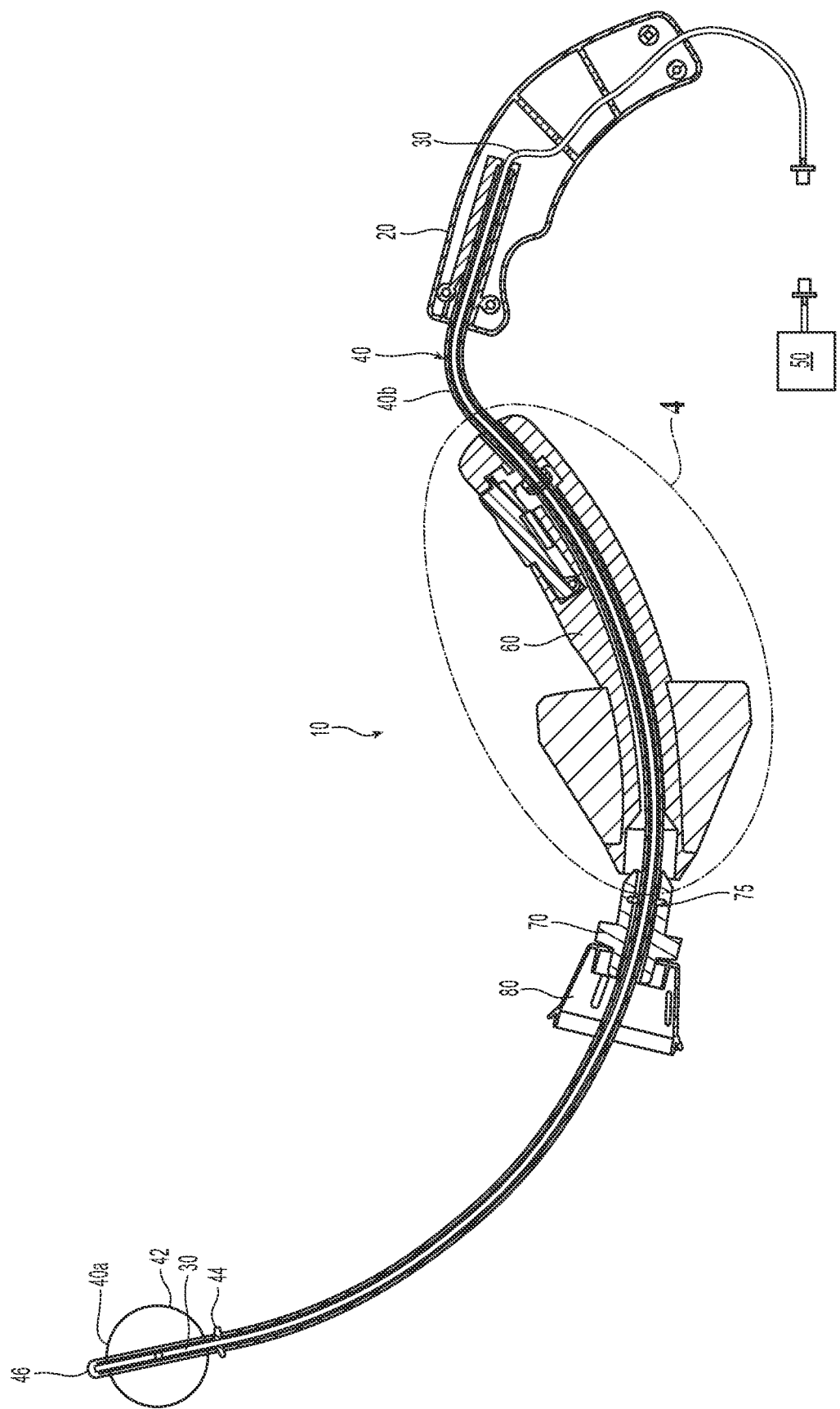
FIG. 2 is an longitudinal, cross-sectional view of the uterine manipulator of FIG. 1.

Turning now to FIGS. 1 and 2, one embodiment of a uterine manipulator, generally referred to as 10, is illustrated. Uterine manipulator 10 defines a center line "X-X" and includes a handle 20 having a proximal end portion 20a and a distal end portion 20b. Handle 20 supports a central shaft 40 and a fluid conduit 30 that extends through handle 20 and central shaft 40. Central shaft 40 includes a proximal end portion 40b and a distal end portion 40a, and has a curvilinear configuration to facilitate transvaginal insertion and cervical and/or uterine positioning. Distal end portion 40a of central shaft 40 extends to a distal tip 46 and supports an inflatable balloon 42 in fluid communication with fluid conduit 30. Fluid conduit 30, which may include one or more fluid conduits of the same and/or different diameters, includes a proximal port 30a (e.g., a luer lock) that couples to an inflation source 50 (e.g., a syringe) for delivering inflation fluid, such as saline, air or the like, to inflatable balloon 42 through fluid conduit 30 for selectively inflating balloon 42 and securing uterine manipulator 10 to uterine tissue. Fluid conduit 30 can support a fluid clamp 32 that is selectively actuatable to inhibit movement of fluid through fluid conduit 30, for example, after fluid is dispensed or injected into, fluid conduit 30 to inflate inflatable balloon 42.

Distal end portion 40a of central shaft 40 further includes a stop collar 44 that extends radially outward from central shaft 40. Stop collar 44 may be in the form of a flange. Each end portion of distal and proximal end portions 40a, 40b of central shaft 40 can include one or more indicia (or series of indicia) such as depth markers (e.g., sequential numbers to indicate depth of insertion—not shown).

As seen in FIG. 1, uterine manipulator 10 further includes an occluder shaft 60, a shuttle 70, and a cervical cup 80 that are each slidably supported on central shaft 40 between proximal and distal positions (e.g., independently relative to one another, and/or collectively as a whole group and/or as a subgroup of shuttle 70, cervical cup 80, and/or occluder shaft 60). Cervical cup 80 may be selectively coupled to shuttle 70 to enable cervical cup 80 and shuttle 70 to move together.

Figure 3:
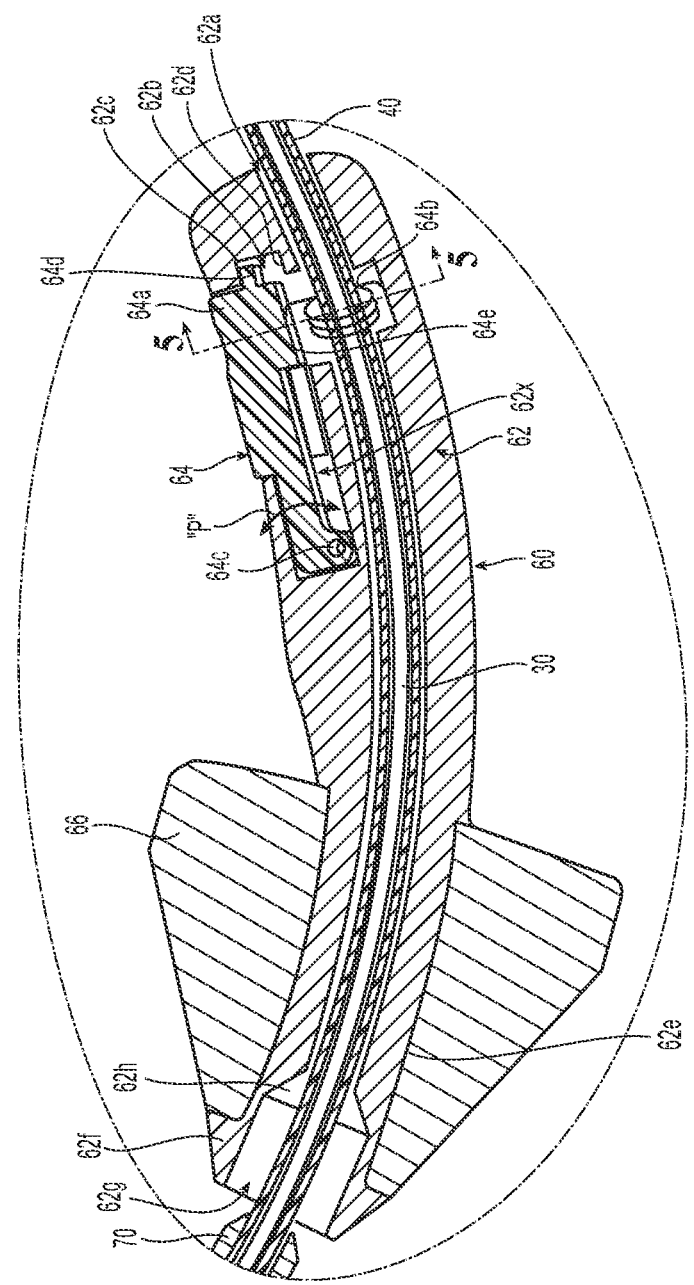
FIG. 3 is an enlarged view of the indicated area of detail shown in FIG. 2.

Turning now to FIG. 3, occluder shaft 60 of uterine manipulator 10 has a proximal end portion that includes a gripping arm 62 and supports a locking mechanism 64, and a distal end portion that includes a plug 66. Occluder shaft 60 defines a central lumen 62a therethrough that slidably receives central shaft 40 of uterine manipulator 10. Gripping arm 62 of occluder shaft 60 is elongated and is shaped and/or configured to enable hand gripping so that a clinician can slide occluder shaft 60 along central shaft 40 between proximal and distal positions, as indicated by arrows "A" (FIG. 1). Gripping arm 62 supports a locking mechanism 64 within a recess 62x defined in a proximal portion of gripping arm 62. Recess 62x of gripping arm 62 includes a tooth slot 62b that is defined by opposing walls 62c, 62d of gripping arm 62. Gripping arm 62 extends to a distal end portion that includes a mounting portion 62e. Mounting portion 62e of gripping arm 62 supports plug 66 and extends to a distal flange 62f that surrounds a distal bore 62g defined therein. Distal bore 62g of mounting portion 62e has tapered proximal portion 62h and is configured to receive shuttle 70 therein.

Figure 5:
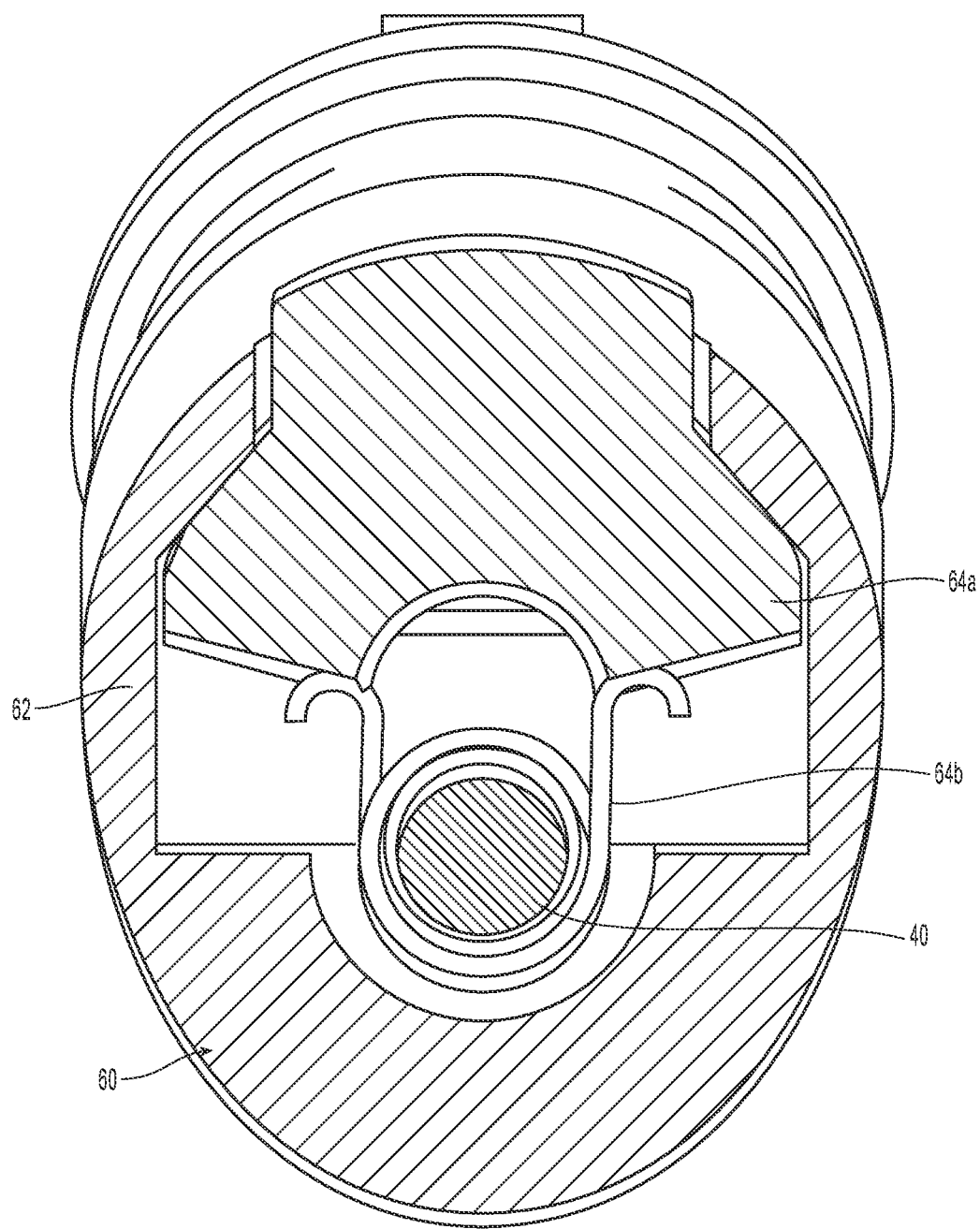
FIG. 5 is a greatly enlarged, perspective, cross-sectional view of the uterine manipulator of FIG. 1, as taken alone section line 5-5 shown in FIG. 3, with a locking mechanism of an occluder shaft of the uterine manipulator shown in a locked position.
Figure 6:
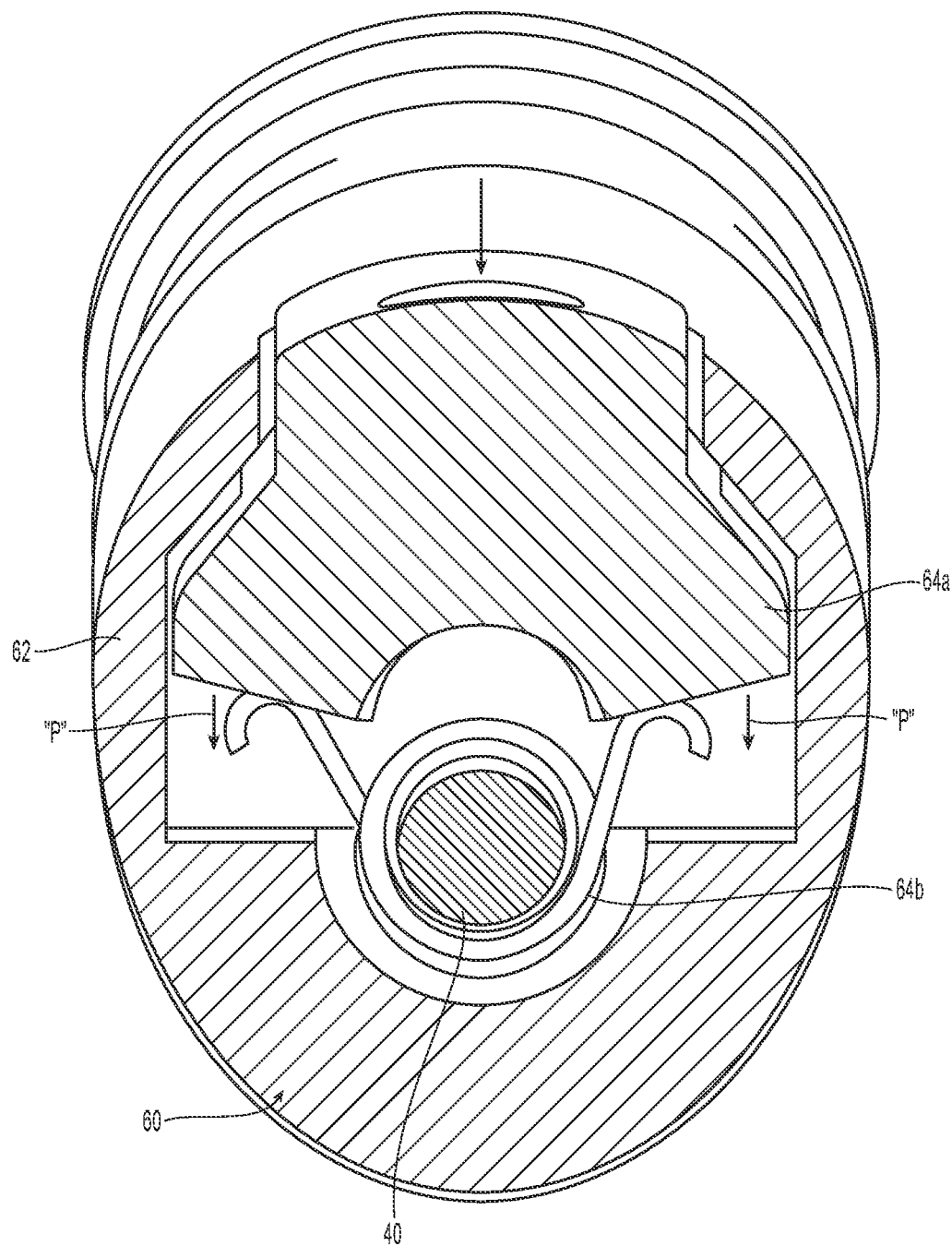
FIG. 6 is a view of FIG. 5 with the locking mechanism of the occluder shaft of FIG. 5 shown in an unlocked position.

Locking mechanism 64 of occluder shaft 60 includes an actuator 64a and a spring 64b (e.g., a torsion spring) that are coupled together to selectively lock occluder shaft 60 to central shaft 40. Actuator 64a of locking mechanism 64 is pivotally coupled to gripping arm 62 at a pivot 64c to enable locking mechanism 64 to pivot between unactuated (FIG. 5) and actuated positions (FIG. 6), as indicated by arrows "P" (FIGS. 3 and 6).

As seen in FIG. 3, pivot 64c of actuator 64a is supported on a distal end portion of actuator 64a, but, in some embodiments, may be supported on a proximal end portion of actuator 64a. Actuator 64a further includes a locking tooth 64d that extends proximally therefrom and is received within tooth slot 62b of recess 62x of gripping arm 62 to limit pivoting movement of locking tooth 64d within tooth slot 62b. In certain embodiments, locking tooth 64d of actuator 64a may extend distally from actuator 64a. Actuator 64a further includes a spring contact surface 64e that contacts spring 64b to selectively impart tension on spring 64b as actuator 64a pivots between unactuated (FIG. 5) and actuated positions (FIG. 6) to move spring 64b between an untensioned position (e.g., uncompressed so as to define a smaller diameter about central shaft 40 to frictionally lock spring 64b to central shaft 40) (FIG. 5) and a tensioned position (e.g., compressed so as to unwind spring 64b and define a larger diameter about central shaft 40 to reduce friction for free sliding of spring 64b along central shaft 40) (FIG. 6). To facilitate use and ease of operation, actuation of actuator 64a can be effectuated, for example, by hand-squeezing actuator 64a while a clinician hand-grips gripping arm 62 of occluder shaft 60.

With continued reference to FIG. 3, plug 66 of occluder shaft 60 tapers distally and may have a frustoconical configuration. In certain embodiments, plug 66 may include various tapers, diameters, and/or geometries to facilitate performance needs. In some embodiments, plug 66 can include a coating, such as a hydrophilic coating to create a lubricious outer layer to reduce friction and facilitate insertion. Plug 66 may include one or more fins (not shown) that extend along an outer surface thereof. Plug 66 may be a non-inflatable occluder (e.g., not a balloon) to provide a quick and easy use and more secure positioning within the vagina as compared to a balloon. Plug 66 may include any suitable biocompatible material such as any suitable polymeric, ceramic, and/or metallic material. Plug 66 may be a solid or semi-solid unitary structure. In some embodiments, plug 66 may include a foam material. Plug 66 may have flexible and/or non-flexible properties. In certain embodiments, plug 66 may have impermeable and/or semi-permeable properties. Plug 66 may be porous and/or non-porous. In certain embodiments, plug 66 may include biologically acceptable additives such as plasticizers, antioxidants, dyes, dilutants, therapeutic agents, and the like, and/or combinations thereof, which can be coated thereon, and/or impregnated therein (e.g., during formation or thereafter). Plug 66 may have any suitable circular or non-circular configuration with any suitable cross-sectional shape such as triangle, square, rectangle, pentagon, etc. In certain embodiments, plug 66 may be a composite structure and/or formed of two or more layers. For a more detailed description of suitable materials and/or additives for use with plug 66, reference can be made to the materials and/or additives of the implants described in U.S. Patent Application Publication No. 2016/0074186 by Sartor and/or in U.S. Pat. No. 8,453,910 to Bettuchi.

Figure 4:
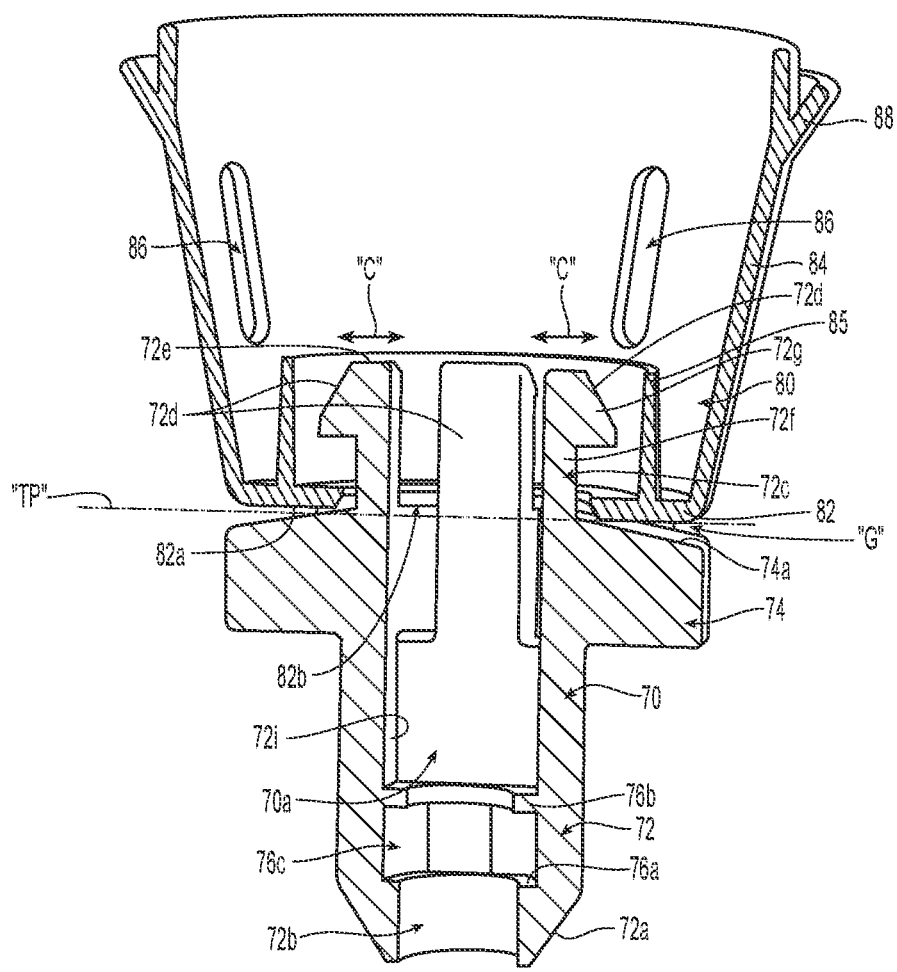
FIG. 4 is an enlarged, longitudinal, cross-sectional view of a cervical cup and shuttle of the uterine manipulator of FIG. 1.

With reference to FIG. 4, shuttle 70 of uterine manipulator 10 includes a tubular body 72 having an annular flange 74 that extends radially outward therefrom and functions as a backstop or proximal abutment for cervical cup 80. Annular flange 74 of shuttle 70 includes a distal face 74a that is angled (e.g., tapers distally) relative to a transverse plane "TP" that extends through shuttle 70 (e.g., orthogonal to centerline "X-X" of central shaft 40). The angled configuration of distal face 74a of annular flange 74 provides an angled gap "G" between a distal surface of annular flange 74 of shuttle 70 and a proximal surface of cervical cup 80 to enable cervical cup 80 to be tilted relative to shuttle 70 and centerline "X-X." Tubular body 72 of shuttle 70 includes an inner surface 72i that defines a central passage 70a through tubular body 72. Central passage 70a receives central shaft 40 (FIG. 1) of uterine manipulator 10 to enable shuttle 70 to slidably move along central shaft 40 between proximal and distal positions, as indicated by arrows "B" (FIG. 1).

Tubular body 72 of shuttle 70 has a proximal end portion 72a that tapers proximally and surrounds a proximal opening 72b defined therein and in fluid communication with, and part of, central passage 70a of shuttle 70. Proximal end portion 72a of tubular body 72 is configured to be removably received within distal bore 62g of occluder shaft 60 (e.g., friction fit, interference fit, slidable fit, etc.). Tubular body 72 of shuttle 70 extends to a distal end portion 72c having one or more flexible tabs 72d (e.g., four) including flexible arms 72f having a distal portion with heads 72g supported thereon. Flexible tabs 72d are circumferentially spaced apart from one another (e.g., angularly displaced 90 degrees apart) around distal end portion 72c and extend distally from annular flange 74 to a distal face 72e. Tabs 72d of tubular body 72 are radially deflectable, as indicated by arrows "C," to releasably attach (e.g., snap-fit) heads 72g of tabs 72d to cervical cup 80. Distal faces 72e of tabs 72d of tubular body 72 function as a backstop that abuts against stop collar 44 of central shaft 40 of uterine manipulator 10 to prevent shuttle 70 of uterine manipulator 10 from sliding off and/or separating from central shaft 40. Inner surface 72i of tubular body 72 includes a proximal inner lip 76a and a distal inner lip 76b that define a bearing recess 76c for supporting a bearing 75 (FIG. 2) between the proximal and distal inner lips 76a, 76b. Bearing 75 facilitates rotational movement of shuttle 70 about central shaft 40 of uterine manipulator 10. In some embodiments, shuttle 70 may be slidably and/or rotatably mounted directly on central shaft 40 without bearing 75. Similar to distal faces 72e of tabs 72d, distal inner lip 76b of shuttle 70 can function as a secondary backstop that can abut against stop collar 44 of central shaft 40 of uterine manipulator 10 to prevent shuttle 70 of uterine manipulator 10 from sliding off and/or separating from central shaft 40.

With continued reference to FIG. 4, cervical cup 80 of uterine manipulator 10 may come in any number of sizes (see e.g., different sized cervical cups shown in FIG. 11) to accommodate patient anatomical differences such as differences in cervical sizes. Cervical cup 80 includes a base wall 82 with an inner annular ledge 82a, and a side wall 84 that extends distally from base wall 82. Annular ledge 82a of base wall 82 defines a central opening 82b through cervical cup 80 that is configured to selectively receive tabs 72d of shuttle 70 therein to enable heads 72g of tabs 72d of shuttle 70 to engage with annular ledge 82a of cervical cup 80. Annular ledge 82a is positioned to obstruct heads 72g of tabs 72d from backing out through central opening 82b unless tabs 72d (e.g., heads 72g of tabs 72d) are depressed radially inward (arrows "C") a sufficient distance to reduce an outer diameter of distal end portion 72c of shuttle 70 to an outer diameter smaller than an outer diameter of central opening 82b of cervical cup 80. With an outer diameter of distal end portion 72c of shuttle 70 reduced, heads 72d of tabs 72d are able to pass through central opening 82b of cervical cup 80 to enable cervical cup 80 to separate from shuttle 70. Base wall 82 of cervical cup 80 includes a raised ring 85 that extends distally from base wall 82 and is positioned to surround tabs 72d of shuttle 70. Raised ring 85 is disposed radially inward of, and spaced from, side wall 84. Raised ring 85 functions to prevent cervical tissue or the like from pushing against tabs 72d of shuttle 70 (to prevent inadvertent depression of tabs 72d) when cervical cup 80 is positioned adjacent cervical tissue during a hysterectomy procedure. Sidewall 84 of cervical cup 80 includes circumferentially spaced-apart elongated openings 86 therethrough that are positioned to receive suture (not shown) therethrough to enable cervical cup 80 to be sutured to tissue. Sidewall 84 further includes an annular rim 88 supported on a distal portion thereof that is configured to guide a cutting device, such as an RF scalpel (not shown), circumferentially about cervical cup 80 to effectuate a colpotomy incision to separate the uterus from the vagina.

Referring now to FIGS. 1-6, in use, a clinician determines a size of a patient's cervix visually or with a tenaculum sizer (not shown) so that the clinician can select an appropriate cervical cup 80 size to be used (see FIG. 11). Once the appropriate size cervical cup 80 is determined and selected, the selected cervical cup 80 is attached to uterine manipulator 10 by sliding cervical cup 80 over distal end portion 40a of central shaft 40 (while inflatable balloon 42 is in an uninflated state—not shown). Cervical cup 80 is then attached to shuttle 70 such that ledge 82a of cervical cup 80 deflects tabs 72d of shuttle 70 radially inward as cervical cup 80 longitudinally approximates shuttle 70 until heads 72g of tabs 72d advance distally beyond ledge 82a so that ledge 82a obstructs heads 72g from moving proximally of ledge 82a and cervical cup 80 is removably coupled to shuttle 70 (FIG. 4). Cervical cup 80 may be removably coupled to shuttle 70 via a loose fit to enable cervical cup 80 to be angled slightly relative to shuttle 70 for providing equal pressure along a vaginal fornix of the patient when cervical cup 80 is advanced forward. If a clinician determines that cervical cup 80 is sized incorrectly, the clinician can swap cervical cup 80 out for another size without disposing of the entire uterine manipulator 10.

With cervical cup 80 of uterine manipulator 10 properly sized, the clinician dilates the patient's cervix with standard reusable GYN dilators (not shown) until central shaft 40 of uterine manipulator 10 can be inserted into the patient's cervix. Tip 46 of central shaft 40 is then inserted into the cervix until tip 46 is sufficiently deep into the uterus. A clinician can note the depth of tip 46 past the cervix by a depth marking (not shown) supported on the distal end portion 40a of central shaft 40 that is visible on central shaft 40 at the cervical opening (e.g., a tip depth measurement).

With inflation source 50 (e.g., a syringe) coupled to fluid conduit 30 via port 30a, inflatable balloon 42 is then inflated inside the uterus (e.g., via fluid injection) to secure uterine manipulator 10 in place. Once inflatable balloon 42 is inflated, fluid clamp 32 is actuated to clamp fluid conduit 30 and prevent the fluid from leaking back out (proximally) of fluid conduit 30 once inflation source 50 is detached.

Cervical cup 80 and shuttle 70 of uterine manipulator 10 is then advanced distally along central shaft 40 of uterine manipulator 10 up to the cervix. The independent motion from occluder shaft 60 enables the clinician to visualize the position of cervical cup 80 on the cervix and also provides access to enable the clinician to suture cervical cup 80 to the cervix if desired for ensured positioning.

The clinician then depresses actuator 64a of locking mechanism 64 to release spring 64b of locking mechanism 64 and distally advance occluder shaft 60 along central shaft 40 until distal bore 62g of occluder shaft 60 mates with proximal end portion 72a of shuttle 70.

As detailed above, central shaft 40 may include one or more depth markers (not shown) adjacent proximal end portion 40b of central shaft 40. In particular, a second series of depth markers (e.g., numbers) may be visible on central shaft 40 proximal to occluder shaft 60. A maker that is visible at the proximal end portion of occluder shaft 60 can indicate a depth measurement that may be configured to correspond to, and/or be consistent with, the tip depth measurement at the cervical opening previously determined to ensure that, during manipulation, tip 46 of central shaft 40 will not be advanced too far, for example, to prevent perforation of the fundus. Actuator 64a of locking mechanism 64 is then released to lock occluder shaft 60 in position on central shaft 40 of uterine manipulator 10.

Plug 66 of occluder shaft 60 of uterine manipulator 10, which may include a compressible foam material, can be compressed during insertion into the vagina such that it expands to its final or resting position behind cervical cup 80 of uterine manipulator 10 to occlude the vaginal canal and prevent loss of pneumoperintoneum once the clinician creates a colpotomy incision.

Handle 20 of uterine manipulator 10 can then be used to manipulate the uterus (antevert, retrovert, lateral motion) while the clinician prepares the uterus laparoscopically (cutting down the blood supply, bladder flap dissection, removing structural ligaments, etc.). The large curvature of central shaft 40 of uterine manipulator 10 provides for a wide range of motion.

The clinician then effectuates a colpotomy incision (e.g., dissects the uterus from the vagina) by using an RF or harmonic scalpel or other cutting device (not shown) positioned up against rim 88 of cervical cup 80 in a circumferential motion. The clinician then removes the uterus (still attached to the uterine manipulator) from the abdomen through the vagina, and the vaginal cuff can be closed via suturing.

Figure 7:
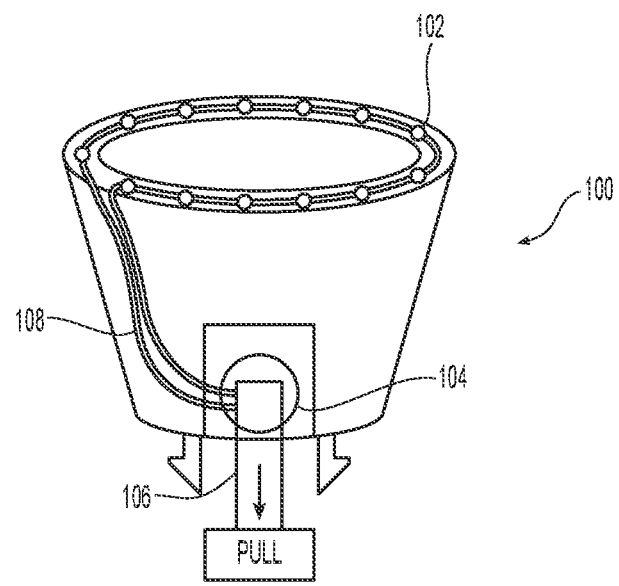
FIG. 7 is a perspective view of one embodiment of a cervical cup of the uterine manipulator of FIG. 1.

Turning now to FIG. 7, one embodiment of a detachable cervical cup, generally referred to as 100, includes a one or more light emitting diodes 102 that are electrically coupled to a battery 104 supported by, or built into, cervical cup 100. Cervical cup 100 can include an insulative tab 106 positioned to obstruct wires 108 within a circuit defined by diodes 102, battery 104, and wires 108 that prevents electrical communication between light emitting diodes 102 and battery until tab 106 is pulled or otherwise separated from the circuit so that diodes 102 electrically communicate with battery 104 to enable diodes 102 to emit light (e.g., wires 108 of the circuit contact battery 104 after tab 106 is pulled).

In some embodiments, an actuatable switch (e.g., a button—not shown) can be provided to selectively complete the circuit to enable battery 104 to selectively illuminate diodes 102 upon actuation of actuatable switch. In certain embodiments, battery 104 may not be built in cervical cup 100, but may be supported, for example, in handle 20 of uterine manipulator 10, (or in any other component of uterine manipulator 10) such that wires 108 are routed through a uterine manipulator (e.g., uterine manipulator 10) to a power source (not shown) supported by, or coupled to, uterine manipulator 10 (e.g. an internally supported battery). In some embodiments, the power source can be an external energy source (e.g., a generator, outlet, and/or external battery).

Figure 8:
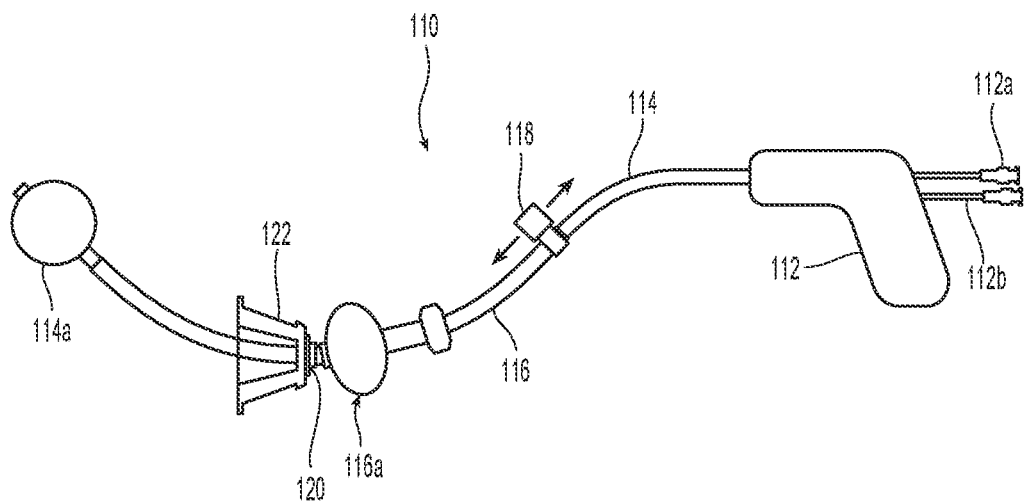
FIG. 8 is a side view of another embodiment of a uterine manipulator in accordance with the principles of the present disclosure.

As seen in FIG. 8, another embodiment of a uterine manipulator is generally referred to as uterine manipulator 110. Uterine manipulator 110 is similar to uterine manipulator 10 and includes a handle 112 having fluid conduits 112a, 112b, a central shaft 114 that extends distally to a first inflatable balloon 114a, an occluder shaft 116 slidably supported on central shaft 114 and extending to a second inflatable balloon 116a (e.g., an occluding balloon that functions similar to plug 66 of uterine manipulator 10), a locking mechanism 118, a hub 120, and a cervical cup 122 mounted to hub 120. First and second inflatable balloons 114a, 116a may be in fluid communication with fluid conduits 112a, 112b for inflation and/or contrast agent, etc.

Figure 9A:
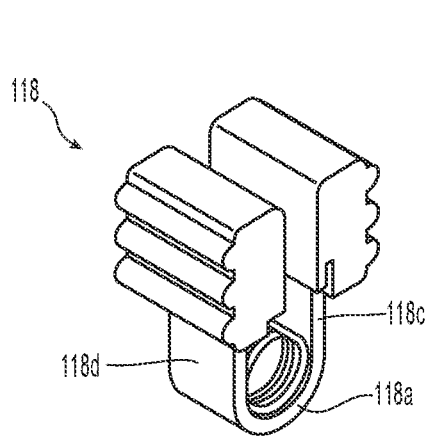
FIG. 9A is a perspective view of another embodiment of a locking mechanism of the uterine manipulator of FIG. 8.
Figure 9B:
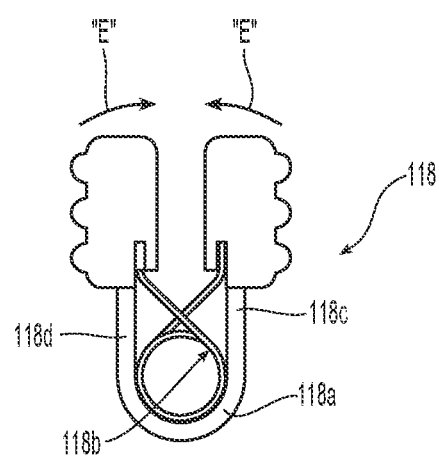
FIG. 9B is a front view of the locking mechanism of FIG. 9A.

With reference to FIGS. 9A and 9B, locking mechanism 118 of uterine manipulator 110 has a U-shaped saddle 118a that supports a spring 118b therein. Saddle 118a includes a first arm 118c and a second arm 118d that extend distally from saddle 118a and are supported for pivoting movement relative to one another, as indicated by arrows "E," to enable selective sliding movement of occluder shaft 116 relative to central shaft 114 between proximal and distal positions along central shaft 114. In particular, in an unactuated (non-squeezed) position (FIG. 9B) of locking mechanism 118, spring 118b frictionally locks to an outer surface of central shaft 114 of uterine manipulator 110 to prevent occluder shaft 116 from sliding along central shaft 114. First and second arms 118c, 118d of locking mechanism 118 support gripping surfaces 118e to facilitate gripping and actuation (e.g., squeezing) of locking mechanism 118.

As seen in FIGS. 10A and 10B, hub 120 of uterine manipulator 110 includes an annular flange 120a to which cervical cup 122 can releasably attach (e.g., snap-fit).

With reference to FIGS. 11-13, uterine manipulator 10 can include a set of cervical cups 130 including any number, size, and/or shape of cups, such as different sized cups 122, 124, 126, etc.

In embodiments, the presently disclosed central shafts 40, 114 may include metallic and/or polymeric materials. In some embodiments, the presently disclosed central shafts 40, 114 may include a coating to facilitate gripping of springs 64b, 118b of the presently disclosed locking mechanisms 64, 118. The coating may include polymeric materials, shrink wrap, rubber, etc. In certain embodiments, the presently disclosed central shafts 40, 114 may include surface texturing such as knurling, ridges, or the like.

Securement of any of the components of the presently disclosed devices may be effectuated using known securement techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A uterine manipulator, comprising:
a central shaft supporting a balloon and a cervical cup;
an occluder shaft movably engaged with the central shaft;
a non-inflatable plug positioned to move with the occluder shaft as the occluder shaft moves along the central shaft; and
a shuttle selectively engaged with the cervical cup and removably received within the non-inflatable plug.

2. The uterine manipulator of claim 1, wherein the cervical cup is selectively detachable from the central shaft.

3. The uterine manipulator of claim 2, wherein the cervical cup includes at least one light emitting diode.

4. The uterine manipulator of claim 1, wherein the occluder shaft slides along an outer surface of the central shaft.

5. The uterine manipulator of claim 1, wherein the shuttle includes at least one tab that is depressible to selectively couple the shuttle to the cervical cup.

6. The uterine manipulator of claim 5, wherein the cervical cup includes a ledge, the at least one tab positioned to engage the ledge of the cervical cup to selectively secure the shuttle and the cervical cup together.

7. The uterine manipulator of claim 6, wherein the cervical cup includes a raised ring that extends from the ledge and is positioned to surround the at least one tab.

8. The uterine manipulator of claim 1, wherein the central shaft includes a collar adjacent to the balloon, the collar positioned to engage the shuttle to prevent the cervical cup from sliding off the central shaft while the cervical cup is coupled to the shuttle.

9. The uterine manipulator of claim 1, further comprising a locking mechanism having a spring supported about the central shaft and positioned to selectively lock the occluder shaft to the central shaft to prevent the occluder shaft from sliding along the central shaft.

10. The uterine manipulator of claim 1, wherein the non-inflatable plug has a tapered configuration that is configured to be received within a vagina to occlude the vagina.

11. A manipulator, comprising:
a central shaft;
a cervical cup;
a shuttle selectively secured to the cervical cup and supported for movement with the cervical cup along the central shaft;
an occluder shaft; and
a plug coupled to the occluder shaft and removably supporting the shuttle therein.

12. The manipulator of claim 11, wherein the plug is positioned to slide along the central shaft independent of the shuttle.

13. The manipulator of claim 11, wherein the occluder shaft slides along an outer surface of the central shaft.

14. The manipulator of claim 11, wherein the plug includes a foam material.

15. The manipulator of claim 11, wherein the plug has a tapered configuration that is configured to be received within a vagina to occlude the vagina.

16. The manipulator of claim 11, wherein the plug has a frustoconical configuration.

17. The manipulator of claim 11, wherein the cervical cup includes at least one light emitting diode.

18. A uterine manipulator, comprising:
a central shaft;
a cervical cup;
a shuttle selectively secured to the cervical cup and supported for movement with the cervical cup along the central shaft;

an occluder shaft supporting a locking mechanism that is configured to prevent relative movement between the occluder shaft and the central shaft; and a plug coupled to the occluder shaft and removably supporting the shuttle therein.

19. The uterine manipulator of claim 18, wherein the locking mechanism supports a torsion spring that prevents the occluder shaft from sliding along the central shaft when the torsion spring is disposed in a first position.

20. The uterine manipulator of claim 19, wherein the locking mechanism includes an actuator coupled to the torsion spring, the actuator positioned for actuation to tension the torsion spring toward a second position, wherein the occluder shaft is positioned to slide along the central shaft when the torsion spring is disposed in the second position.

* * * * *